(12) United States Patent
Lorenz et al.

(10) Patent No.: US 9,994,672 B2
(45) Date of Patent: Jun. 12, 2018

(54) HYDROXY-AMINOPOLYMERS AND METHOD FOR PRODUCING SAME

(71) Applicant: Bayer Intellectual Property GmbH, Monheim (DE)

(72) Inventors: Klaus Lorenz, Dormagen (DE); Jorg Hofmann, Krefeld (DE); Hartmut Nefzger, Pulheim (DE)

(73) Assignee: Covestro Deutschland AG, Leverkusen (DE)

( * ) Notice: Subject to any disclaimer, the term of this patent is extended or adjusted under 35 U.S.C. 154(b) by 0 days. days.

(21) Appl. No.: 14/366,342

(22) PCT Filed: Dec. 17, 2012

(86) PCT No.: PCT/EP2012/075819
§ 371 (c)(1),
(2) Date: Jun. 18, 2014

(87) PCT Pub. No.: WO2013/092501
PCT Pub. Date: Jun. 27, 2013

(65) Prior Publication Data
US 2014/0329972 A1   Nov. 6, 2014

(30) Foreign Application Priority Data
Dec. 20, 2011 (EP) ..................... 11194419

(51) Int. Cl.
| | | |
|---|---|---|
| *C08G 65/26* | (2006.01) | |
| *C08G 63/91* | (2006.01) | |
| *C08G 18/10* | (2006.01) | |
| *C08G 18/38* | (2006.01) | |
| *C08G 18/42* | (2006.01) | |
| *C08G 18/46* | (2006.01) | |
| *A61K 8/81* | (2006.01) | |

(52) U.S. Cl.
CPC .............. *C08G 63/91* (2013.01); *C08G 18/10* (2013.01); *C08G 18/3821* (2013.01); *C08G 18/4252* (2013.01); *C08G 18/4615* (2013.01); *A61K 8/817* (2013.01); *A61K 8/8147* (2013.01)

(58) Field of Classification Search
CPC .. A61K 8/8147; A61K 8/817; C08G 65/2663; C08G 18/12; C08G 18/48
USPC .......... 525/440, 447, 449; 528/291
See application file for complete search history.

(56) References Cited

U.S. PATENT DOCUMENTS

| | | |
|---|---|---|
| 4,874,837 A | 10/1989 | Bershas et al. |
| 5,476,892 A | 12/1995 | Scholl et al. |
| 5,508,312 A | 4/1996 | Munzmay et al. |
| 5,554,687 A | 9/1996 | Yang |
| 5,597,390 A | 1/1997 | Loper |
| 5,734,002 A | 3/1998 | Reich et al. |
| 5,739,192 A | 4/1998 | Blizzard et al. |
| 5,770,671 A | 6/1998 | Nefzger et al. |
| 5,977,284 A | 11/1999 | Reich et al. |
| 5,998,327 A | 12/1999 | Hofmann et al. |
| 6,020,283 A | 2/2000 | Rosthauser et al. |
| 6,020,386 A | 2/2000 | Munzmay et al. |
| 6,093,793 A | 7/2000 | Hofmann et al. |
| 6,140,381 A | 10/2000 | Rosthauser et al. |
| 6,177,144 B1 | 1/2001 | Kranig et al. |
| 6,204,357 B1 | 3/2001 | Ooms et al. |
| 6,291,388 B1 | 9/2001 | Hofmann et al. |
| 6,323,375 B1 | 11/2001 | Hofmann et al. |
| 6,361,843 B1 | 3/2002 | Smith et al. |
| 6,391,820 B1 | 5/2002 | Ooms et al. |
| 6,407,201 B1 | 6/2002 | Taylor et al. |
| 6,444,720 B1 | 9/2002 | Klesczewski et al. |
| 6,458,918 B1 | 10/2002 | Schafer et al. |
| 6,468,939 B1 | 10/2002 | Ooms et al. |
| 6,472,447 B1 | 10/2002 | Lorenz et al. |
| 6,482,993 B1 | 11/2002 | Hofmann et al. |
| 6,486,361 B1 | 11/2002 | Ehlers et al. |
| 6,492,565 B2 | 12/2002 | Denninger et al. |
| 6,528,616 B1 | 3/2003 | Ooms et al. |
| 6,541,411 B2 | 4/2003 | Hoffmann et al. |
| 6,586,566 B1 | 7/2003 | Hofmann et al. |
| 6,608,231 B1 | 8/2003 | Doms et al. |
| 6,617,419 B1 | 9/2003 | Hofman et al. |
| 6,624,286 B2 | 9/2003 | Hofmann et al. |
| 6,646,100 B2 | 11/2003 | Hofmann et al. |
| 6,670,406 B2 | 12/2003 | Hofmann et al. |
| 6,737,471 B2 | 5/2004 | Lorenz et al. |
| 6,780,813 B1 | 8/2004 | Hofmann et al. |

(Continued)

FOREIGN PATENT DOCUMENTS

| | | |
|---|---|---|
| EP | 1493767 A1 | 1/2005 |
| JP | 04089860 A | 3/1992 |
| WO | 2010090345 A1 | 8/2010 |

*Primary Examiner* — Gregory Listvoyb
(74) *Attorney, Agent, or Firm* — N. Denise Brown; Richard P. Bender

(57) ABSTRACT

The present invention relates to a process for the preparation of a hydroxy-amino polymer, comprising the steps: a) reacting an H-functional starter compound carrying at least one Zerewitinoff-active H atom with an unsaturated cyclic carboxylic acid anhydride and at least one alkylene oxide compound to give a hydroxyl-group-carrying prepolymer, b) adding a primary amine and/or ammonia to the double bonds of the hydroxyl-group-carrying prepolymer obtained according to step a) to give the hydroxy-amino polymer, wherein the reaction of the H-functional starter compound with the unsaturated cyclic carboxylic acid anhydride and/or the addition of the alkylene oxide compound is carried out using a double metal cyanide catalyst (DMC catalyst). The invention relates additionally to a hydroxy-amino polymer obtainable by the above-mentioned process, wherein the ratio of the amount of alkylene oxide compound to the amount of carboxylic acid anhydride is at least 1.1:1, and further to the use of this hydroxy-amino polymer in the preparation of a polyurethane urea polymer.

15 Claims, No Drawings

(56) References Cited

U.S. PATENT DOCUMENTS

| | | |
|---|---|---|
| 6,852,663 B2 | 2/2005 | Ooms et al. |
| 6,858,655 B1 | 2/2005 | Hofmann et al. |
| 6,858,699 B2 | 2/2005 | Michels et al. |
| 6,878,661 B1 | 4/2005 | Ooms et al. |
| 6,919,293 B1 | 7/2005 | Ooms et al. |
| 6,953,765 B2 | 10/2005 | Ooms et al. |
| 6,977,290 B2 | 12/2005 | Nefzger et al. |
| 7,008,900 B1 | 3/2006 | Hofmann et al. |
| 7,091,304 B2 | 8/2006 | Nefzger et al. |
| 7,763,683 B2 | 7/2010 | Nefzger et al. |
| 7,772,330 B2 | 8/2010 | Lorenz et al. |
| 7,893,150 B2 | 2/2011 | Nefzger et al. |
| 7,893,189 B2 | 2/2011 | Lorenz et al. |
| 2002/0120028 A1 | 8/2002 | Lorenz et al. |
| 2004/0064001 A1 | 4/2004 | Ehlers et al. |
| 2005/0124733 A1 | 6/2005 | Nefzger et al. |
| 2005/0131137 A1 | 6/2005 | Nefzger et al. |
| 2005/0137275 A1 | 6/2005 | Nefzger et al. |
| 2005/0171002 A1 | 8/2005 | Mohanty et al. |
| 2006/0004172 A1 | 1/2006 | Nefzger et al. |
| 2006/0047011 A1 | 3/2006 | Kusan-Bindels et al. |
| 2006/0111513 A1 | 5/2006 | Slansky et al. |
| 2006/0135727 A1 | 6/2006 | Nefzger et al. |
| 2006/0205912 A1 | 9/2006 | Nefzger et al. |
| 2006/0211830 A1 | 9/2006 | Lorenz et al. |
| 2007/0010593 A1 | 1/2007 | Nefzger et al. |
| 2007/0010643 A1 | 1/2007 | Nefzger et al. |
| 2007/0049720 A1 | 3/2007 | Krause et al. |
| 2007/0049721 A1 | 3/2007 | Nefzger et al. |
| 2007/0123725 A1 | 5/2007 | Lorenz |
| 2007/0135608 A1 | 6/2007 | Hannig et al. |
| 2007/0265367 A1* | 11/2007 | Le-Khac et al. ................ 522/96 |
| 2008/0047824 A1 | 2/2008 | Nefzger et al. |
| 2008/0114086 A1 | 5/2008 | Lorenz et al. |
| 2008/0146695 A1 | 6/2008 | Nefzger et al. |
| 2008/0177025 A1 | 7/2008 | Hofmann |
| 2008/0300377 A1 | 12/2008 | Nefzger et al. |
| 2008/0306176 A1 | 12/2008 | Nefzger et al. |
| 2009/0018256 A1 | 1/2009 | Nefzger et al. |
| 2009/0131606 A1 | 5/2009 | Schmidt et al. |
| 2010/0086861 A1 | 4/2010 | Weiser et al. |
| 2010/0125126 A1 | 5/2010 | Lorenz et al. |
| 2010/0190995 A1 | 7/2010 | Lui et al. |
| 2011/0021738 A1 | 1/2011 | Lorenz |
| 2011/0133598 A1 | 6/2011 | Jenninger et al. |
| 2011/0230581 A1 | 9/2011 | Klescewski et al. |
| 2011/0306734 A1 | 12/2011 | Brauer et al. |

* cited by examiner

HYDROXY-AMINOPOLYMERS AND METHOD FOR PRODUCING SAME

CROSS-REFERENCE TO RELATED APPLICATION

This application is a National Phase application to PCT/EP2012/075819, filed Dec. 17, 2012 and European Application No.: 11194419.5, filed Dec. 20, 2011.

FIELD OF THE INVENTION

The present invention relates to hydroxy-amino polymers, to a process for their preparation, and to the use of such hydroxy-amino polymers in the preparation of polyurethane ureas.

BACKGROUND

Polymers which are both amine-functional and carry hydroxyl groups (so-called hydroxy-amino polymers) are increasingly of interest in some fields of application, especially in the field of the polyurethane industry. The reason for this is that the presence of two different types of functional groups, namely the amine functionalities and the hydroxyl groups, enables novel property and processing profiles to be achieved. For example, combining the amino groups, which are significantly more reactive towards isocyanate groups, with the less reactive hydroxyl groups gives rise to the possibility of influencing the progress of curing processes over time in a desirable manner, which has hitherto not been possible or has been possible to only a limited extent in the presence of only one type of the above-mentioned isocyanate-reactive functional groups.

In general, the amino functionality of hydroxy-amino polymers can be introduced into macromolecules by the addition of primary amines or ammonia to low-electron double bonds, for example of the (meth)acylate type. The addition of amines to (meth)acrylate-group-containing polymers, inter alia to (meth)acrylate-group-containing polyethers, is known per se; such processes are mentioned, for example, in U.S. Pat. No. 5,739,192 A1, U.S. Pat. No. 5,597,390 A1, US 2005/0171002 A1, DE 196 16 984 A1, DE 195 08 308 A1, WO 2010/090345 A1, JP 2009/22753 A1 and JP 04089860 A1.

By contrast, the obtainment of the precursor compounds comprising the low-electron double bonds in the prior art is either not described or takes place via condensation reactions that proceed according to the laws of statistics, for example by the esterification of acrylic acid with difunctional polyethers or the reaction of acryloyl chloride with difunctional polyethers.

A common feature of all the described processes is that the introduction of double bonds into the precursor compounds of the hydroxy-amino polymers takes place at the expense of the number of hydroxy functions. Accordingly, these processes do not allow the original hydroxy functionality, which in the case of polyether molecules is generally given by the functionality of the starter molecules used to prepare the polyethers, to be retained during the introduction of the amino functions.

Processes as are described, for example, in U.S. Pat. No. 4,874,837 A1 solve this problem in part by reacting mixtures of maleic anhydride and further anhydrides with the hydroxy groups of low molecular weight polyether polyols, converting the resulting acid groups of the semiesters back into hydroxy groups by addition of alkylene oxides, and introducing the amine function by addition of amino alcohols comprising primary or secondary amino groups or diamines comprising primary or secondary amino groups at the reactive double bonds of the hydroxy maleate.

A structural disadvantage of the hydroxy-amino polyether esters prepared in that manner is that the hydroxy groups and the amino groups are at a fixed and small distance of from 6 to 7 covalent bond lengths from one another and only one amino group can be introduced per hydroxy group. This situation can be shown schematically as follows:

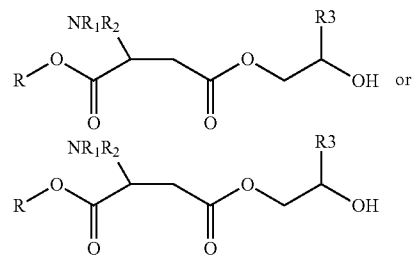

where R=polyether radical, R1, R2=radicals (hydrogen or alkyl) on the nitrogen atom, and R3=radical (hydrogen or alkyl on the alkylene oxide used to convert the acid groups into hydroxy groups)

The two above-mentioned products of the Michael addition of the amine to the double bond are present in more or less equal parts, yielding a mixture of polymers with 6 and 7 bond lengths between the hydroxy group and the amino group.

U.S. Pat. No. 5,554,687 discloses a process in which α,β-unsaturated dicarboxylic acids or their anhydrides are first esterified by polyhydric alcohols or alkylene oxides to give an unsaturated "polyol polyester prepolymer". In the case of maleic anhydride as the α,β-unsaturated dicarboxylic acid, the esterification is preferably to be carried out in the presence of morpholine as isomerisation catalyst. The specification does not mention further catalysts for the esterification process. In the presence of morpholine (an aminic catalyst), maleic anhydride reacts with alkylene oxides such that precisely one alkylene oxide structural unit is incorporated between two maleic anhydride structural units. When ethylene oxide is used as the alkylene oxide, there is thus ultimately obtained a polyester as from the reaction of maleic acid with ethylene glycol.

The "polyol polyester prepolymer" (a) is then reacted in a second step with a polyoxyalkyleneamine (b) in a weight ratio (a)(b) of from 0.8 to 50 to give an amine-containing polyester resin. There are disclosed as polyoxyalkyleneamines (b) polymers of polyether blocks with amino end groups, for example $H_2N$—$CHXCH_2$—$[OCH_2CHX]_n$—$NH_2$, wherein X represents hydrogen or an alkyl group having from 1 to 18 carbon atoms and n is a natural number from 2 to 70. The terminal amino groups are added to the double bonds of the polyol polyester prepolymer. There are thus ultimately obtained crosslinked polyester resins in which the polyester chains are linked together via polyamino bridges. A process for the preparation of hydroxy-amino polymers in the sense of amino-group-containing poly(ether)ester polyols is neither described in nor rendered obvious by U.S. Pat. No. 5,554,687. Moreover, the process of U.S. Pat. No. 5,557,687 is subject to the same limitations as U.S. Pat. No. 4,874,837 A1 in relation to the structure of the chain ends. The distance between the terminal hydroxy group and the first amino group can here likewise be a maximum of 7 covalent bond lengths.

Accordingly, the object of the present invention was to provide a process for the preparation of hydroxyl-amino polymers which on the one hand permits the creation of hydroxy-amino polymers having a distance of more than seven covalent bond lengths between the amino functionality and the hydroxy functionality; on the other hand, the possibility of incorporating more than only one amine group per OH group into the polymer is to be opened up, this process is further to be simple to apply and, moreover, is to avoid as far as possible the formation of secondary products, such as, for example, transesterification products, so that working up of the process products is generally not necessary.

SUMMARY

The object is achieved by a process for the preparation of a hydroxy-amino polymer comprising the steps:
a) reacting an H-functional starter compound carrying at least one Zerewitinoff-active H atom with an unsaturated cyclic carboxylic acid anhydride and at least one alkylene oxide compound to give a hydroxyl-group-carrying prepolymer,
b) adding a primary amine and/or ammonia to the double bonds of the hydroxyl-group-carrying prepolymer obtained according to step a) to give the hydroxy-amino polymer,
wherein the reaction of the H-functional starter compound with the unsaturated cyclic carboxylic acid anhydride and/or the addition of the alkylene oxide compound is carried out using a double metal cyanide catalyst (DMC catalyst).

DETAILED DESCRIPTION

The indefinite article "a", "an" is to be understood as meaning that in each case also a plurality of these components may be reacted with one another in the process according to the invention.

A "hydroxy-amino polymer" within the meaning of the present invention is a poly(ether)ester polyol comprising amino groups, that is to say a polymer comprising amino groups, in which polyether polyol sequences are linked together via dicarboxylic acid functionalities.

Surprisingly, it has been found that the above-mentioned hydroxy-amino polymers are obtainable by adding amines to hydroxyl-group-carrying prepolymers obtainable by reaction of at least one Zerewitinoff-active H atom of an H-functional starter compound with an unsaturated cyclic carboxylic acid anhydride and at least one alkylene oxide compound with double metal cyanide (DMC) catalysis. The process can be so controlled that, in addition to the hydroxy-amino polymers known hitherto having at least a distance of six or seven covalent bond lengths between the amino function and the hydroxyl group, structures that have a distance of greater than 7 covalent bond lengths can also be prepared.

The process can also be so configured, for example, that, after a metered alkylene oxide compound has reacted completely, unsaturated cyclic carboxylic acid anhydride is fed in, for example approximately 1 mol of carboxylic acid anhydride per mol of OH groups present. Then, a desired amount of alkylene oxide compounds is again added in order to obtain the hydroxyl-group-carrying prepolymer. The above-mentioned reaction sequence can also be repeated one or more times, so that a desired number of double bonds, in particular more than one double bond, can be incorporated into the polymer per Zerewitinoff-active H atom. In that manner, for example, 2 or more, in particular 3 or more, amino functionalities can finally be introduced per Zerewitinoff-active H atom by addition to the double bonds. Naturally, the double bonds can also be introduced into the prepolymer by the parallel metering of one or more alkylene oxide compounds and one or more unsaturated cyclic carboxylic acid anhydrides into the starter compounds carrying one or more Zerewitinoff-active atoms. The distribution of the double bonds onto the polymer chains of the prepolymer then takes place according to the laws of statistics; in particular, the blocks of the polyether chains based on alkylene oxide structural units are subject to a broader length distribution.

Within the context of the present invention it is provided that the H-functional starter compound carries at least one Zerewitinoff-active H atom. A Zerewitinoff-active H atom is understood within the context of the present invention as being an acidic H atom or "active" H atom. Such an atom can be identified in a manner known per se by reactivity with a corresponding Grignard reagent. The amount of Zerewitinoff-active H atoms is typically measured by the amount of methane liberated when the substance to be tested is reacted with methylmagnesium bromide ($CH_3$—MgBr) according to the following reaction equation:

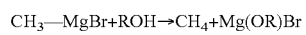

$CH_3$—MgBr+ROH→$CH_4$+Mg(OR)Br

Zerewitinoff-active H atoms typically originate from C—H acidic organic groups, —OH, —SH, —$NH_2$ or —NHR where R is an organic radical, and —COOH.

Particularly suitable H-functional starter compounds possess an H functionality of from 1 to 35, in particular from 1 to 16, preferably from 1 to 8, the H functionality being based on the above-mentioned Zerewitinoff-active H atoms.

The molecular weights of the H-functional starter compounds can vary over wide ranges, a mean molecular weight of from 17 to 1200 g/mol being particularly preferred, in particular from 62 to 1000.

In addition to the hydroxy-functional starters that are preferably to be used, amino-functional starters can also be employed.

Examples of hydroxy-functional starter compounds are methanol, ethanol, 1-propanol, 2-propanol and higher aliphatic monols, in particular fatty alcohols, phenol, alkyl-substituted phenols, propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerol, trimethylolpropane, pentaerythritol, sorbitol, sucrose, hydroquinone, pyrocatechol, resorcinol, bisphenol F, bisphenol A, 1,3,5-trihydroxybenzene, as well as methylol-group-containing condensation products of formaldehyde and phenol or urea. It is also possible to use highly functional starter compounds based on hydrogenated starch hydrolysis products. Such compounds are described, for example, in EP 1525244 A1.

Examples of amino-group-containing H-functional starter compounds are ammonia, ethanolamine, diethanolamine, triethanolamine, isopropanolamine, diisopropanolamine, ethylenediamine, hexamethylenediamine, aniline, the isomers of toluidine, the isomers of diaminotoluene, the isomers of diaminodiphenylmethane and higher nuclear products formed in the condensation of aniline with formaldehyde to give diaminodiphenylmethane, also methylol-group-containing condensation products of formaldehyde and melamine as well as Mannich bases.

Moreover, ring-opening products of cyclic carboxylic acid anhydrides and polyols can also be used as starter compounds. Examples are ring-opening products of phthalic anhydride or succinic anhydride on the one hand and ethylene glycol, diethylene glycol, 1,2-butanediol, 1,3-butanediol, 1,4-butanediol, hexanediol, pentanediol, 3-methyl-1,5-pentanediol, 1,12-dodecanediol, glycerol, trimethylolpropane, pentaerythritol or sorbitol on the other hand. In addition, it is also possible to use mono or polyfunctional carboxylic acids directly as starter compounds.

Furthermore, pre-produced alkylene oxide addition products of the mentioned starter compounds, that is to say polyether polyols preferably having OH numbers of from 160 to 1000 mg KOH/g, preferably from 250 to 1000 KOH/g, can also be used in the process as starter compounds or added to the reaction mixture. It is also possible to use polyester polyols preferably having OH numbers in the range of from 6 to 800 mg KOH/g as co-starters in the process according to the invention. Polyester polyols suitable therefor can be prepared, for example, by known processes from organic dicarboxylic acids having from 2 to 12 carbon atoms and polyhydric alcohols, preferably diols, having from 2 to 12 carbon atoms, preferably from 2 to 6 carbon atoms.

There can further be used as H-functional starter substances polycarbonate polyols, polyester carbonate polyols or polyether carbonate polyols, preferably polycarbonate diols, polyester carbonate diols or polyether carbonate diols, preferably in each case having OH numbers in the range of from 6 to 800 mg KOH/g, as starters or co-starters. These are prepared, for example, by reaction of phosgene, dimethyl carbonate, diethyl carbonate or diphenyl carbonate with di- or higher-functional alcohols or polyester polyols or polyether polyols.

In step a) of the process according to the invention there are preferably used amino-group-free H-functional starter compounds with hydroxy groups as carriers of the active hydrogens, such as, for example, methanol, ethanol, 1-propanol, 2-propanol and higher aliphatic monols, in particular fatty alcohols, phenol, alkyl-substituted phenols, propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerol, trimethylolpropane, pentaerythritol, sorbitol, sucrose, hydroquinone, pyrocatechol, resorcinol, bisphenol F, bisphenol A, 1,3,5-trihydroxybenzene, methylol-group-containing condensation products of formaldehyde and phenol and hydrogenated starch hydrolysis products. Mixtures of different H-functional starter compounds can also be used. Any mention in the following of an H-functional starter compound also includes in principle mixtures of H-functional starter compounds, unless this is expressly excluded.

For the unsaturated cyclic carboxylic acid anhydride used within the scope of the process according to the invention there are suitable all compounds known as such to the person skilled in the art. These are, for example, unsaturated cyclic dicarboxylic acid anhydrides, such as maleic anhydride, tetrahydrophthalic anhydride, in particular 3,4,5,6-tetrahydrophthalic anhydride, and combinations thereof.

If a plurality of unsaturated cyclic carboxylic acid anhydrides is used, they can likewise be metered in individually, in a mixture or block-wise. It is additionally possible to feed the cyclic carboxylic acid anhydride or the cyclic carboxylic acid anhydrides to the reaction mixture in parallel with the alkylene oxide(s) or as a separate block, without simultaneous alkylene oxide metering. Any mention in the following of an unsaturated cyclic carboxylic acid anhydride also includes in principle mixtures of unsaturated cyclic carboxylic acid anhydrides, unless this is expressly excluded.

As the alkylene oxide compound which can be used according to the invention there can be chosen those representatives which contain from 2 to 24 carbon atoms, in particular from 2 to 12 carbon atoms, more preferably from 2 to 6 carbon atoms, as well as the combination of different alkylene oxide compounds of the above-mentioned type. Alkylene oxides having from 2 to 24 carbon atoms are, for example, one or more compounds selected from the group consisting of ethylene oxide, propylene oxide, 1-butene oxide, 2,3-butene oxide, 2-methyl-1,2-propene oxide (isobutane oxide), 1-pentene oxide, 2,3-pentene oxide, 2-methyl-1,2-butene oxide, 3-methyl-1,2-butene; oxide, 1-hexene oxide, 2,3-hexene oxide, 3,4-hexene oxide, 2-methyl-1,2-pentene oxide, 4-methyl-1,2-pentene oxide, 2-ethyl-1,2-butene oxide, 1-heptene oxide, 1-octene oxide, 1-nonene oxide, 1-decene oxide, 1-undecene oxide, 1-dodecene oxide, 4-methyl-1,2-pentene oxide, butadiene monoxide, isoprene monoxide, cyclopentene; oxide, cyclohexene oxide, cycloheptene oxide, cyclooctene oxide, styrene oxide, methylstyrene oxide, pinene oxide, mono- or poly-epoxidised fats as mono-, di- and tri-glycerides, epoxidised fatty acids, $C_1$-$C_{24}$-esters of epoxidised fatty acids, epichlorohydrin, glycidol and derivatives of glycidol such as, for example, methyl glycidyl ether, ethyl glycidyl ether, 2-ethylhexyl glycidyl ether, allyl glycidyl ether, glycidyl methacrylate, as well as epoxide-functional alkyloxysilanes such as, for example, 3-glycidyloxypropyltrimethoxysilane, 3-glycidyloxypropyltriethoxysilane, 3-glycidyloxypropyltripropoxysilane, 3-glycidyloxypropyl-methyl-dimethoxysilane, 3-glycidyloxypropylethyldiethoxysilane and 3-glycidyloxypropyltriisopropoxysilane.

The alkylene oxides used for the preparation of the polyether ester polyols in step a) are preferably ethylene oxide and/or propylene oxide. The alkylene oxides can be metered in individually, in a mixture or block-wise. Any mention in the following of an alkylene oxide or an alkylene oxide compound in principle includes also mixtures of alkylene oxides or alkylene oxide compounds or the block-wise metering of different alkylene oxides or alkylene oxide compounds, unless expressly specified.

Preferably, ethylene oxide and/or propylene oxide are used. Particularly preferably, ethylene oxide is used in amounts greater than 50 wt. %, most particularly preferably in amounts greater than 60 wt. %, based on the total mass of the alkylene oxides to be metered in. It can further be provided in the process according to the invention that the ratio of the amount of carboxylic acid anhydride to the number Zerewitinoff-active H atoms of the starter compound is so chosen that all the Zerewitinoff-active H atoms are reacted if possible. For this stoichiometric reaction, the ratio of the amount of carboxylic acid anhydride to the number of Zerewitinoff-active H atoms of the H-functional starter compound can be approximately from 1:1 to 1.5:1, in particular from 1:1 to 1.2:1.

According to a particularly preferred embodiment of the process according to the invention, the ratio of the amount of alkylene oxide compound to the amount of carboxylic acid anhydride is adjusted to at least 1.1:1, preferably to at least 2:1, particularly preferably at least to 2.5:1. In this embodiment of the process according to the invention, it is possible to synthesise hydroxy-amino polymers having a mean distance of more than seven covalent bond lengths between the amine functionality and the hydroxyl group.

Moreover, the process according to the invention is not limited to the use of the above-mentioned monomers or comonomers. For example, it is possible for at least one further comonomer to be reacted in step a), which comonomer is selected in particular from lactones, lactides, saturated or aromatic cyclic carboxylic acid anhydrides, cyclic carbonates and/or carbon dioxide. In this manner, the property profile of the resulting hydroxy-amino polymer can be further modified, for example in respect of its reactivity to isocyanate groups, its polarity, and in terms of other chemical or physical properties of the hydroxy-amino polymer or its reaction product with a polyisocyanate.

Within the context of the process according to the invention it is provided inter alia that a primary amine or ammonia is added to the double bond of the hydroxyl-group-carrying prepolymer. Suitable amines are, for example, ammonia, aliphatic, cycloaliphatic and/or araliphatic monoamines having a primary amino group such as, for example, methylamine, ethylamine, 1-aminopropane, 2-aminopropane, 1-aminobutane, 2-aminobutane, isobutylamine, 1-aminohexane, 2-ethyl-1-aminohexane, dodecylamine, octadecylamine, cyclohexylamine and benzylamine; aliphatic, cycloaliphatic, and/or araliphatic monoamines having a primary amino group and a secondary amino group, wherein the secondary amino group may also be part of a ring system, such as, for example, N-methylethylenediamine, N-methylpropylenediamine, N-(2-aminoethyl)-piperazine and 3-amino-1,2,4-triazole; aliphatic, cycloaliphatic and/or heterocyclic diamines having a primary and a tertiary amino group and optionally a secondary amino group such as, for example, N,N-dimethylethylenediamine, N,N-dimethyl-1,3-diaminopropane, N,N-dimethyl-1,8-diaminooctane, N,N-dimethyl-1,4-diaminocyclohexane; and aliphatic diamines having two primary and at least one secondary amino group, such as, for example, diethylenetriamine, triethylenetetramine, tetraethylenepentamine and bis-(3-aminopropyl)-amine. Furthermore, amities that also comprise hydroxy groups in addition to the primary amino group, such as, for example, ethanolamine or isopropanolamine, are suitable for the process according to the invention. Preference is given to primary amities selected from the group consisting of ethylamine, 1-aminobutane, dodecylamine, cyclohexylamine, benzylamine, N,N-dimethyl-1,3-diaminopropane, ethanolamine and isopropanolamine.

Also suitable are (cyclo)aliphatic diamines. These are compounds having two primary amino groups with the general formula $NH_2-R-NH_2$, in which R represents an aliphatic or cycloaliphatic radical having from 2 to 21, preferably from 2 to 15 and particularly preferably from 2 to 10 carbon atoms. Examples which may be mentioned are ethylenediamine, 1,2- and 1,3-propylenediamine, 1,4-diaminobutane, 1,6-diaminohexane, 2,2,4- and 2,4,4-trimethyl-1,6-diaminohexane, 1,4-diaminocyclohexane, 1,5-diamino-2-methylpentane, 5-amino-1-aminomethyl-1,3,3-trimethylcyclohexane (isophoronediamine), bis-(4-aminocyclohexyl)-methane, bis-(4-amino-3-methylcyclohexyl)-methane, 1-amino-1-methyl-3(4)-aminomethylcyclohexane, bis-(4-amino-3,5-diethylcyclohexyl)-methane, bis-aminomethyl-hexahydro-4,7-methano-indane, 2,3-, 2,4- and 2,6-diamino-1-methylcyclohexane or mixtures of these diamines. Preference is given to (cyclo)aliphatic diamines selected from the group consisting of ethylenediamine, 1,4-diaminobutane, 1,6-diaminohexane, 1,5-diamino-2-methylpentane, bis-(4-aminocyclohexyl)-methane and bis-(4-amino-3-methylcyclohexyl)-methane.

The mentioned mono- and oligo-amines can of course also be used in the form of a mixture. Any mention in the following of an amine to be added in principle includes also mixtures of amines to be added, unless expressly specified.

The molar ratio of primary amino groups to double bonds capable of addition is preferably from 0.01:1 to 1.1:1, preferably from 0.1:1 to 1.1:1, particularly preferably from 0.5:1 to 1.1:1 and most particularly preferably from 1:1 to 1.1:1. The reaction can be carried out with or without catalysis. Suitable catalysts are, for example, copper acetate, tin chloride or acetic acid. The addition of the amines is preferably carried out without the addition of a catalyst. A reaction temperature range suitable for this step is, for example, the range from 0° C. to 150° C., preferably from 10° C. to 100° C. and particularly preferably from 20° C. to 80° C.

In the process according to the invention it is provided that a DMC catalyst is used in step a), that is to say in the reaction of the H-functional starter compound with the unsaturated cyclic carboxylic acid anhydride and/or the addition of the alkylene oxide compound. Mixtures of different DMC catalysts can also be used.

Suitable DMC catalysts are known in principle from the prior art and are disclosed, for example, in U.S. Pat. No. 3,404,109 A1, U.S. Pat. No. 3,829,505 A1, U.S. Pat. No. 3,941,849 A1 and U.S. Pat. No. 5,158,922 A1.

DMC catalysts described, for example, in U.S. Pat. No. 5,470,813 A1, EP 700949 A1, EP 743 093 A1, EP 761 708 A1, WO 97/40086 A1, WO 98/16310 A1 and WO 00/47649 A1 possess very high activity in the polymerisation of alkylene oxides and optionally the copolymerisation of alkylene oxides and unsaturated cyclic carboxylic acid anhydrides and permit the preparation of polyether polyols at very low catalyst concentrations (25 ppm or less), so that the separation of the catalyst from the finished product is generally no longer necessary. A typical example is the highly active DMC catalysts described in EP 700 949 A1 which, as well as comprising a double metal cyanide compound such as zinc hexacyanocobaltate(III) and an organic complex ligand such as tert-butanol, also comprise a polyether having a number-average molecular weight greater than 500 g/mol. It is also possible to use the alkaline DMC catalysts disclosed in EP application number 10163170.3.

Cyanide-free metal salts suitable for the preparation of the double metal cyanide compounds preferably have the general formula (I)

$$M(X)_n \qquad (I)$$

wherein

M is selected from the metal cations $Zn^{2+}$, $Fe^{2+}$, $Ni^{2+}$, $Mn^{2+}$, $Co^{2+}$, $Sn^{2+}$, $Pb^{2+}$ and $Cu^{2+}$, M is preferably $Zn^{2+}$, $Fe^{2+}$, $Co^{2+}$ or $Ni^{2+}$, X represents one or more (i.e. different) anions, preferably selected from the group of the halides (i.e. fluoride, chloride, bromide, iodide), hydroxide, sulfate, carbonate, cyanate, thiocyanate, isocyanate, isothiocyanate, carboxylate, oxalate and nitrate;

n is 1 when X=sulfate, carbonate or oxalate, and n is 2 when X=halide, hydroxide, cyanate, thiocyanate, isocyanate, isothiocyanate or nitrate.

Further suitable cyanide-free metal salts have the general formula (II)

$$M_r(X)_3 \qquad (II)$$

wherein

M is selected from the metal cations $Fe^{3+}$, $Al^{3+}$ and $Cr^+$,

X represents one or different anion types, the anion preferably being selected from the group of the halides (i.e. fluoride, chloride, bromide, iodide), hydroxide, sulfate, carbonate, cyanate, thiocyanate, isocyanate, isothiocyanate, carboxylate, oxalate and nitrate, r is 2 when X=sulfate, carbonate or oxalate, and
r is 1 when X=halide, hydroxide, cyanate, thiocyanate, isocyanate, isothiocyanate, carboxylate or nitrate.

Other suitable cyanide-free metal salts have the general formula (III)

$$M(X)_s \qquad (III)$$

wherein
M is selected from the metal cations $Mo^{4+}$, $V^{4+}$ and $W^{4+}$,
X represents one or different anion types, the anion preferably being selected from the group of the halides (i.e. fluoride, chloride, bromide, iodide), hydroxide, sulfate, carbonate, cyanate, thiocyanate, isocyanate, isothiocyanate, carboxylate, oxalate and nitrate;
s is 2 when X=sulfate, carbonate or oxalate, and
s is 4 when X=halide, hydroxide, cyanate, thiocyanate, isocyanate, isothiocyanate, carboxylate or nitrate.

Cyanide-free metal salts that are likewise suitable have the general formula (IV)

$$M(X)_t \qquad (IV)$$

wherein
M is selected from the metal cations $Mo^{6+}$ and $W^{6+}$,
X represents one or different anion types, the anion preferably being selected from the group of the halides (i.e. fluoride, chloride, bromide, iodide), hydroxide, sulfate, carbonate, cyanate, thiocyanate, isocyanate, isothiocyanate, carboxylate, oxalate and nitrate;
t is 3 when X=sulfate, carbonate or oxalate, and
t is 6 when X=halide, hydroxide, cyanate, thiocyanate, isocyanate, isothiocyanate, carboxylate or nitrate.

Examples of suitable cyanide-free metal salts are zinc chloride, zinc bromide, zinc iodide, zinc acetate, zinc acetylacetortate, zinc benzoate, zinc nitrate, iron(II) sulfate, iron (II) bromide, iron(II) chloride, cobalt(II) chloride, cobalt(II) thiocyanate, nickel(II) chloride and nickel(H) nitrate. Mixtures of different metal salts can also be used.

Metal cyanide salts suitable for the preparation of the double metal cyanide compounds preferably have the general formula (V)

$$(Y)_a M'(CN)_b (A)_c \qquad (V)$$

wherein
M' is selected from one or more metal cations from the group consisting of Fe(III), Co(II), Co(III), Cr(II), Cr(III), Mn(II), Mn(III), Ir(III), Ni(II), Rh(III), Ru(II), V(IV) and V(V), M' is preferably one or more metal cations from the group consisting of Co(II), Co(III), Fe(II), Fe(III), Cr(III), Ir(III) and Ni(II),
Y is selected from one or more metal cations from the group consisting of alkali metal (i.e. $Li^+$, $Na^+$, $K^+$, $Rb^+$, $Cs^+$) and alkaline earth metal (i.e. $Be^{2+}$, $Ca^{2+}$, $Mg^{2+}$, $Sr^{2+}$, $Ba^{2+}$),
A is selected from one or more anions from the group consisting of halides (i.e. fluoride, chloride, bromide, iodide), hydroxide, sulfate, carbonate, cyanate, thiocyanate, isocyanate, isothiocyanate, carboxylate, oxalate or nitrate, and
a, b and c are integers, the values for a, b and c being so chosen that the electroneutrality of the metal cyanide salt is given; a is preferably 1, 2, 3 or 4; b is preferably 4, 5 or 6; c preferably has the value 0.

Examples of suitable metal cyanide salts are potassium hexacyanocobaltate(III), potassium hexacyanoferrate(II), potassium hexacyanoferrate(III), calcium hexacyanocobaltate(III) and lithium hexacyanocobaltate(III).

Preferred double metal cyanide compounds which are contained in the DMC catalysts according to the invention are compounds of the general formula (VI)

$$M_x[M'_{x'}(CN)_y]_z \qquad (VI)$$

wherein M is as defined in formulae (I) to (IV) and
M' is as defined in formula (V), and
x, x', y and z are integers and are so chosen that the electroneutrality of the double metal cyanide compound is given.

Preferably,
x=3, x'=1, y=6 and z=2,
M=Zn(II), Fe(II), Co(II) or Ni(II) and
M'=Co(III), Fe(III), Cr(III) or Ir(III).

Examples of double metal cyanide compounds which are preferably used are zinc hexacyanocobaltate(III), zinc hexacyanoiridate(III), zinc hexacyanoferrate(III) and cobalt (II) hexacyanocobaltate(III). Further examples of suitable double metal cyanide compounds are to be found, for example, in U.S. Pat. No. 5,158,922 A1 Zinc hexacyanocobaltate(III) is particularly preferably used.

The organic complex ligands added in the preparation of the DMC catalysts are disclosed, for example, in U.S. Pat. No. 5,158,922 A1, U.S. Pat. No. 3,404,109 A1, U.S. Pat. No. 3,829,505 A1, U.S. Pat. No. 3,941,849 A1, EP 700949 A1, EP 761708 A1, JP 4145123 A1, U.S. Pat. No. 5,470,813 A1, EP 743 093 A1 and WO 97/40086 A1. For example, there are used as organic complex ligands water-soluble, organic compounds with heteroatoms, such as oxygen, nitrogen, phosphorus or sulfur, which are able to form complexes with the double metal cyanide compound. Preferred organic complex ligands are alcohols, aldehydes, ketones, ethers, esters, amides, ureas, nitrites, sulfides and mixtures thereof. Particularly preferred organic complex ligands are aliphatic ethers (such as dimethoxyethane), water-soluble aliphatic alcohols (such as ethanol, isopropanol, n-butanol, isobutanol, sec-butanol, tert-butanol, 2-methyl-3-buten-2-ol and 2-methyl-3-butyn-2-ol), compounds which contain both aliphatic or cycloaliphatic ether groups and aliphatic hydroxyl groups (such as, for example, ethylene glycol mono-tert-butyl ether, diethylene glycol mono-tert-butyl ether, tripropylene glycol monomethyl ether and 3-methyl-3-oxetan-methanol). Most preferred organic complex ligands are selected from one or more compounds from the group consisting of dimethoxyethane, tert-butanol, 2-methyl-3-buten-2-ol, 2-methyl-3-butyn-2-ol, ethylene glycol mono-tert-butyl ether and 3-methyl-3-oxetan-methanol.

In the preparation of the DMC catalysts that are preferred according to the invention there are optionally used one or more complex-forming component(s) from the compound classes of the polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylic acid-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly (N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethylcellulose and polyacetals, or of the glycidyl ethers, glycosides, carboxylic acid esters of polyhydric alcohols, gallic acids or salts, esters or amides thereof, cyclodextrins, phosphorus compounds, α,β-unsaturated carboxylic acid esters or ionic surface-active compounds.

In the preparation of the DMC catalysts that are preferred according to the invention there are preferably reacted in the first step the aqueous solutions of the metal salt (e.g. zinc chloride), used in stoichiometric excess (at least 50 mol %) based on metal cyanide salt (that is to say at least a molar ratio of cyanide-free metal salt to metal cyanide salt of from 2.25 to 1.00) and of the metal cyanide salt (e.g. potassium hexacyanocobaltate) in the presence of the organic, complex ligand (e.g. tert-butanol), so that a suspension forms which contains the double metal cyanide compound (e.g. zinc hexacyanocobaltate), water, excess cyanide-free metal salt, and the organic complex ligand. The organic complex ligand can be present in the aqueous solution of the cyanide-free metal salt and/or of the metal cyanide salt, or it is added directly to the suspension obtained after precipitation of the double metal cyanide compound. It has been found to be advantageous to mix the aqueous solutions of the cyanide-free metal salt and of the metal cyanide salt and the organic complex ligand with vigorous stirring. Optionally, the suspension formed in the first step is then treated with a further complex-forming component. The complex-forming component is preferably used in a mixture with water and organic complex ligand. A preferred process for carrying out the first step (i.e. the preparation of the suspension) takes place using a mixing nozzle, particularly preferably using a jet disperser as described in WO 01/39883 A1.

In the second step, the solid (i.e. the precursor of the catalyst according to the invention) is isolated from the suspension by known techniques, such as centrifugation or filtration.

In a preferred variant for the preparation of the catalyst, the isolated solid is then washed in a third process step with an aqueous solution of the organic complex ligand (e.g. by being resuspended and then isolated again by filtration or centrifugation). In this manner, water-soluble secondary products, for example, such as potassium chloride, can be removed from the catalyst according to the invention. Preferably, the amount of organic complex ligand in the aqueous wash solution is from 40 to 80 wt. %, based on the total solution.

Optionally, a further complex-forming component, preferably in the range from 0.5 to 5 wt. %, based on the total solution, is added to the aqueous wash solution in the third step.

It is additionally advantageous to wash the isolated solid more than once. To that end, the first washing operation can be repeated, for example. However, it is preferred to use non-aqueous solutions for further washing operations, for example a mixture of organic complex ligand and further complex-forming component.

The isolated and optionally washed solid is then, optionally after pulverisation, dried at temperatures of generally from 20 to 100° C. and at pressures of generally from 0.1 mbar to normal pressure (1013 mbar).

A preferred process for isolating the DMC catalysts according to the invention from the suspension by filtration, filter cake washing and drying is described in WO 01/80994 A1.

The concentration of DMC catalyst used in step a) is from 5 to 1000 ppm, preferably from 10 to 900 ppm and particularly preferably from 20 to 800 ppm, based on the amount of the hydroxyl-group-carrying prepolymer to be prepared. Depending on the requirements profile of the use following the amine addition, the DMC catalyst can be left in the product or (partially) separated off. (Partial) separation of the DMC catalyst can be carried out, for example, by treatment with adsorbents. Processes for separating off DMC catalysts are described, for example, in U.S. Pat. No. 4,987,271 A1, DE 313 22 58 A1, EP 406 440 A1, U.S. Pat. No. 5,391,722 A1, U.S. Pat. No. 5,099,075 A1, U.S. Pat. No. 4,721,818 A1, U.S. Pat. No. 4,877,906 A1 and EP 385 619 A1.

Before the H-functional starter compound is brought into contact with the DMC catalyst, small amounts of an inorganic mineral acid, preferably phosphoric acid, can be added to the H-functional compound in order to neutralise any traces of base in the H-functional starter compound.

If the process according to the invention is carried out using double metal cyanide catalysts, it is further advantageous first to place the H-functional starter compound and the catalyst in a reaction vessel, to meter in a partial amount of the alkylene oxide compound and optionally further comonomers, and only then to add the unsaturated cyclic carboxylic acid anhydride. In this manner, a double-bond-free polymer skeleton can first be constructed starting from the H-functional starter compound. All of the above-mentioned alkylene oxide compounds and optionally additional comonomers can be used for that purpose. The unsaturated cyclic carboxylic acid anhydride is typically fed to the reaction mixture when the above-mentioned addition reaction of the alkylene oxide compound to the H-functional starter compound is complete.

After the unsaturated cyclic carboxylic acid anhydride has been added, the alkylene oxide compound, and optionally further comonomer, is then added again. The distance between the amine functionality and the hydroxyl group can thereby be adjusted as described above by the choice of the amounts of the alkylene oxide compound(s) in relation to the amount of added unsaturated carboxylic acid anhydride, there being added in particular more than 1 mol of the alkylene oxide compound per mol of Zerewitinoff-active hydrogen. The distance of those two functionalities from one another can also be influenced by addition of further comonomer. As already mentioned above, further carboxylic acid anhydride and, when it has reacted completely, further alkylene oxide compound can then be added in order to provide the possibility of incorporating more than one amine function per Zerewitinoff-active H atom.

Step a) of the process according to the invention will be described in detail below, the present invention not being limited to the following description:

In one embodiment of the process according to the invention, the H-functional compound is first placed in the reactor/reactor system with the DMC catalyst. Before the H-functional compound is brought into contact with the DMC catalyst, small amounts of an inorganic mineral acid, preferably phosphoric acid, can optionally be added to the H-functional compound in order to neutralise any traces of base in the H-functional starter compound or in order to make the process generally more stable.

After heating to temperatures of from 50 to 160° C., in particular from 60 to 140° C., most particularly preferably from 70 to 140° C., the contents of the reactor, in a preferred process variant, are stripped with inert gas over a period of preferably from 10 to 60 minutes, with stirring. In the stripping with inert gas, volatile constituents are removed by passing inert gases into the liquid phase while at the same time applying a vacuum, at an absolute pressure of from 5 to 500 mbar. After the metering in of typically from 5 to 20 wt. % of one or more alkylene oxides, optionally already comprising a small amount of the unsaturated cyclic carboxylic acid anhydride and/or further comonomer, based on the amount of H-functional compound placed in the reactor, the DMC catalyst is activated.

The addition of one or more alkylene oxides and optionally of a small amount of the unsaturated cyclic carboxylic acid anhydride and/or further comonomer can occur before, during or after the heating of the contents of the reactor to temperatures of from 50 to 160° C., preferably from 60 to 140° C., particularly preferably from 70 to 140° C.; it is preferably carried out after stripping. Activation of the catalyst manifests itself in an accelerated drop in the reactor pressure, which indicates the start of the alkylene oxide conversion/conversion of the unsaturated cyclic carboxylic acid anhydride.

The desired amount of alkylene oxide or alkylene oxide mixture, optionally together with the amount of unsaturated cyclic carboxylic acid anhydride and/or further comonomer that is to be metered in, can then be fed continuously to the reaction mixture, a reaction temperature of from 20 to 200° C., but preferably from 50 to 160° C. being chosen. The reaction temperature is in many cases identical with the activation temperature. Before the unsaturated cyclic carboxylic acid anhydride is metered in, an inhibitor such as, for example, a phenol derivative, vitamin E phenothiazine can optionally be added to the reaction mixture or the H-functional compound.

Activation of the catalyst often takes place so quickly that the metering in of a separate amount of alkylene oxide/of the unsaturated cyclic carboxylic acid anhydride for catalyst activation can be omitted and the continuous metering in of the alkylene oxide and of the unsaturated cyclic carboxylic acid anhydride can be started directly, optionally at a reduced metering rate at first. The reaction temperature can also be varied within the described limits during the alkylene oxide metering phase/metering of the unsaturated cyclic carboxylic acid anhydride. The alkylene oxides and the cyclic carboxylic acid anhydride can also be fed to the reactor in different ways: Metering into the gas phase or directly into the liquid phase, for example via an immersion pipe or a distributor ring located in a well-mixed zone close to the bottom of the reactor, is possible.

In DMC-catalysed processes, metering into the liquid phase is the preferred variant.

The alkylene oxide and the unsaturated cyclic carboxylic acid anhydride should be fed continuously to the reactor in such a manner that the safety-related pressure limits of the reactor system used are not exceeded. In particular in the case of the co-metering of ethylene-oxide-containing alkylene oxide mixtures or pure ethylene oxide, it must be ensured that a sufficient inert gas partial pressure is maintained in the reactor during the start-up and metering phase. This can be established, for example, by means of noble gases or nitrogen.

In the case of metering into the liquid phase, the metering units should be designed to be self-emptying, for example by attaching the metering bores to the bottom of the distributor ring. In general, the back-flow of reaction medium into the metering units and starting material reservoirs should be prevented by apparatus-related measures, for example by the fitting of non-return valves. If an alkylene oxide/carboxylic acid anhydride mixture is metered, the alkylene oxides in question and the unsaturated cyclic carboxylic acid anhydrides in question can be fed to the reactor separately or in the form of a mixture. Pre-mixing of the alkylene oxides with one another and with the unsaturated cyclic carboxylic acid anhydride can be achieved, for example, by a mixing unit located in the common metering line ("inline blending"). It has also been found to be advantageous to meter alkylene oxides and optionally the unsaturated cyclic carboxylic acid anhydride, individually or in pre-mixed form, on the pump pressure side into a recirculation loop guided, for example, via heat exchangers. For thorough mixing with the reaction medium, it is then advantageous to integrate a high-shear mixing unit into the alkylene oxide/carboxylic acid anhydride/reaction medium stream. The temperature of the exothermic ring-opening addition reaction is kept at the desired level by cooling. According to the prior art relating to the design of polymerisation reactors for exothermic reactions (e.g. Ullmann's Encyclopedia of industrial Chemistry, Vol. B4, pp. 167 ff, 5th Ed., 1992), such cooling generally takes place via the reactor wall (e.g. double-walled jacket, half-pipe coil) as well as by means of further heat exchanger surfaces arranged internally in the reactor and/or externally in the recirculation loop, for example at cooling coils, cooling plugs, plate, tube bundle or mixer heat exchangers. These should be so designed that effective cooling can be achieved even at the start of the metering phase, that is to say with a small filling level.

In general, thorough mixing of the contents of the reactor should be ensured in all phases of the reaction by the configuration and use of conventional stirring elements, there being suitable here in particular stirrers arranged in one or more stages or stirrer types that act over a large area over the filling height (see e.g. Handbuch Apparate; Vulkan-Verlag Essen, 1st Ed, (1990), p. 188-208). Of particular technical relevance here is mixing energy introduced on average over the entire reactor contents, which mixing energy is generally in the range from 0.2 to 5 W/l, with correspondingly higher local energy inputs in the region of the stirring elements themselves and optionally at low filling levels. In order to achieve an optimum stirring action, combinations of baffles (e.g. flat or tubular baffles) and cooling coils (or cooling plugs), which may also extend over the bottom of the vessel, can be arranged according to the general prior art in the reactor. The stirring efficiency of the mixing unit can also be varied during the metering phase in dependence on the filling level, in order to ensure a particularly high energy input in critical phases of the reaction. For example, it may be advantageous to mix solids-containing dispersions, which can be present at the beginning of the reaction, for example, when sucrose is used, particularly intensively.

Moreover, in particular when using solid H-functional starter compounds, it should be ensured, by the choice of stirring unit, that the dispersion of the solid in the reaction mixture is sufficient. There are preferably used here bottom-based stirring stages and stirring elements suitable in particular for suspension. Furthermore, the stirrer geometry should contribute towards reducing the foaming of reaction products. The foaming of reaction mixtures can be observed, for example, after the end of the metering and post-reaction phase when residual epoxides are additionally removed in vacuo at absolute pressures in the range of from 1 to 500 bar. Stirring elements that achieve continuous thorough mixing of the liquid surface have been found to be particularly suitable for such cases. Depending on the requirement, the stirrer shaft has a bottom bearing and optionally further support bearings in the vessel. The stirrer shaft can be driven from the top or bottom (with the shaft arranged centrally or eccentrically).

Alternatively, it is also possible to achieve the necessary thorough mixing solely by means of a recirculation loop guided via heat exchangers, or to operate this in addition to the stirring unit as a further mixing component, the contents of the reactor being recirculated as required (typically from 1 to 50 times per hour).

Very different types of reactor are suitable for carrying out the process according to the invention. Preferably, cylindrical vessels having a height/diameter ratio of from 1:1 to 10:1 are used. Suitable reactor bottoms are, for example, spherical, dished, flat or conical bottoms.

The metering of the alkylene oxide and of the unsaturated cyclic carboxylic anhydride and optionally further comonomers in step a) can be followed by a post-reaction phase in which residual alkylene oxide/unsaturated cyclic carboxylic acid anhydride/further comonomer is reacted to completion. The end of this post-reaction phase is reached when no further pressure drop can be detected in the reaction vessel. Traces of unreacted alkylene oxides/unsaturated cyclic carboxylic acid anhydrides can be removed quantitatively after the reaction phase optionally in vacuo at an absolute pressure of from 1 to 500 mbar or by stripping. By stripping, volatile constituents, such as, for example, (residual) alkylene oxides, are removed by passing inert gases or water vapour into the liquid phase while at the same time applying a vacuum (for example by passing through inert gas at an absolute pressure of from 5 to 500 mbar). The removal of volatile constituents, such as, for example, unreacted epoxides, either in vacuo or by stripping is carried out at temperatures of from 20 to 200° C., preferably at from 50 to 160° C., and preferably with stirring. Such stripping operations can also be carried out in so-called stripping columns, in which a stream of inert gas or water vapour is passed countercurrently to the product stream. Stripping with inert gases is preferably carried out in the absence of water vapour. After a constant pressure has been reached, or after volatile constituents have been removed by vacuum and/or stripping, the product can be discharged from the reactor.

In process variant A), the metering of the cyclic carboxylic acid anhydride in step a) can also be carried out in such a manner that the alkylene oxide metering/metering of further comonomers is interrupted and, optionally after a post-reaction phase, the unsaturated cyclic carboxylic acid anhydride is fed to the reactor and, after feeding of the desired amount of unsaturated cyclic carboxylic acid anhydride, the alkylene oxide metering/metering of further comonomers is resumed. This procedure can of course also be repeated several times during one reaction batch. It is particularly preferred in this procedure that the final alkylene oxide block comprises an amount of greater than 1 mol of alkylene oxide per mol of active H atoms from the H-functional compounds used as starter compounds. Here too, an inhibitor such as, for example, a phenol derivative, vitamin E or phenothiazine can optionally be added to the reaction mixture or the H-functional compound before the unsaturated cyclic carboxylic acid anhydride is metered in.

Continuous or stepwise variation of the ratio of the metering rates of the alkylene oxide metering and the metering of the unsaturated cyclic carboxylic acid anhydride during the metering phase, that is to say the common metering of those two components, is also possible, for example in that the ratio of the metered stream of the unsaturated cyclic carboxylic acid anhydride to that of the alkylene oxide/alkylene oxides assumes values of from 0:1 to 1:0.

A characteristic of DMC catalysts is their pronounced sensitivity to high concentrations of hydroxyl groups, which are caused, for example, by large amounts of starters such as ethylene glycol, propylene glycol, glycerol, trimethylolpropane, sorbitol or sucrose, and polar impurities of the reaction mixture or of the starter or starters. The DMC catalysts cannot then be converted into the polymerisation-active form during the reaction initiation phase. Impurities can be, for example, water or compounds having a large number of hydroxyl groups in close proximity, such as carbohydrates and carbohydrate derivatives. Substances having carbonyl groups in close proximity or carbonyl groups adjacent to hydroxyl groups also adversely affect the catalyst activity.

In order nevertheless to be able to subject starters with high concentrations of OH groups, or starters with impurities that are to be considered as catalytic poisons, to DMC-catalysed alkylene oxide addition reactions, the hydroxyl group concentration should be reduced, or the catalytic poisons should be rendered harmless. To that end, prepolymers can first be prepared from those starter compounds by means of basic catalysis, which prepolymers, after working up, are then converted into the desired alkylene oxide addition products of high molar mass by means of DMC catalysis. These prepolymers include, for example, the above-mentioned "pre-produced alkylene oxide addition products" that are suitable as starters. This procedure has the disadvantage that such prepolymers often obtained by means of basic catalysis must be worked up very carefully in order to exclude deactivation of the DMC catalyst by traces of basic catalyst introduced via the prepolymers.

This disadvantage can be overcome by the so-called process of continuous starter metering, in which critical starter compounds are not placed in the reactor but are fed continuously to the reactor together with the alkylene oxides during the reaction. Prepolymers can be placed in the reactor in this process as the starter medium for the reaction, and it is also possible to use as the starter medium small amounts of the product that is to be prepared. The necessity of first separately preparing prepolymers that are suitable for further alkylene oxide additions is thus avoided.

In variant B) of step a) of the process according to the invention, therefore, a starter polyol and the DMC catalyst are placed in the reaction system, and the H-functional compound is fed in continuously together with the alkylene oxide and the unsaturated cyclic carboxylic acid anhydride. Suitable as the starter polyol in step a) are alkylene oxide addition products such as, for example, polyether polyols, polyester polyols, polyether ester polyols, polycarbonate polyols, polyester carbonate polyols, polyether carbonate polyols, in each case having for example, OH numbers in the range of from 3 to 1000 mg KOH/g, preferably from 3 to 300 mg KOH/g, and/or intermediate product prepared separately according to step a). Intermediate product prepared separately according to step a) is preferably used as the starter polyol in step a).

In a less preferred variant of this embodiment B), continuous or stepwise variation of the ratio of the metering rates of the alkylene oxide metering and the metering of the unsaturated cyclic carboxylic acid anhydride is also possible during the metering phase of the three components, in that, for example, the ratio of the metered stream of the unsaturated cyclic carboxylic acid anhydride to that of the alkylene oxide/epoxides assumes values of from 0:1 to 1:0. This embodiment is less preferred because it yields the intermediate product according to step a) in a less homogeneous form.

In embodiment B) of step a), the metering of the H-functional compound and the metering of the alkylene oxide as well as of the unsaturated cyclic carboxylic acid anhydride is preferably terminated simultaneously, or the H-functional compound and a first partial amount of alkylene oxide and a first partial amount of the unsaturated cyclic carboxylic acid anhydride are first metered in together, and then the second partial amount of alkylene oxide and unsaturated cyclic carboxylic acid anhydride is metered in, the sums of the first and second partial amounts of alkylene oxide and the first and second partial amounts of unsaturated cyclic carboxylic acid anhydride corresponding to the total amount of one or more alkylene oxides or one or more unsaturated cyclic carboxylic acid anhydrides used in step a). The first partial amount is preferably from 60 to 98 wt. % and the second partial amount is from 40 to 2 wt. % of the total amount of alkylene oxide to be metered in in step a). The first partial amount is preferably from 0 to 100 wt. % and the second partial amount is from 100 to 0 wt. % of the total amount of one or more unsaturated cyclic carboxylic acid anhydrides to be metered in in step a).

If the composition of the alkylene oxides and/or the composition/metering rate of the one or more unsaturated cyclic carboxylic acid anhydrides is changed after the end of the metering of the H-functional compound, products with multi-block structures can also be prepared according to process variant B). In process variant B) too, it is preferred that the metering of the unsaturated cyclic carboxylic acid anhydride is terminated before the alkylene oxide metering, particularly preferably such that this terminal alkylene oxide block comprises an amount of greater than 1 mol of alkylene oxide per mol of active H atoms from the H-functional compounds used as starter compounds. The metering of the reagents can be followed by a post-reaction phase, in which the consumption of alkylene oxide/unsaturated cyclic carboxylic acid anhydride can be quantified by monitoring the pressure. When a constant pressure has been reached, the product can be discharged, optionally after application of vacuum or by stripping to remove unreacted alkylene oxides, as described above.

In variant C) of step a) of the process according to the invention, the intermediate products can be prepared wholly continuously. To that end, the DMC catalyst is fed continuously to the reactor or a reactor system under alkoxylation conditions together with alkylene oxide and the H-functional compound as well as the unsaturated cyclic carboxylic acid anhydride, and the product is continuously removed from the reactor or reactor system after a preselectable mean residence time. In process variant C), it is preferred to use as the reactor system a reactor cascade in which a third, continuously operated reactor is located between the post-reactor and the actual reactor, into which third reactor only the one or more alkylene oxides are continuously metered. In a particularly preferred embodiment of process variant C), the terminal alkylene oxide block comprises an amount of greater than 1 mol of alkylene oxide per mol of active H atoms from the H-functional compounds used as starter compounds.

Continuous post-reaction steps may follow, for example in a reactor cascade or in a tubular reactor. Volatile constituents can be removed in vacuo and/or by stripping, as described above.

The OH numbers of the hydroxyl group-containing prepolymer obtained according to the DMC-catalysed addition step a) preferably have values of from 3 mg KOH/g to 200 mg KOH/g, particularly preferably from 10 to 60 mg KOH/g, most particularly preferably from 20 to 50 mg KOH/g.

The OH number can be determined, for example, titrimetrically as specified in DIN 53240 or spectroscopically by NIR.

The equivalent molar mass is to be understood as being the total mass of the material containing active hydrogen atoms divided by the number of active hydrogen atoms. In the case of hydroxy-group-containing materials, it is related to the OH number as follows:

Equivalent molar mass=56,100/OH number [mg KOH/g]

Anti-ageing agents such as, for example, antioxidants can optionally be added to the intermediate products obtainable according to step a) of the process according to the invention.

Step b) of the process according to the invention will be described in detail below. This description is also given by way of example and is not to be interpreted as limiting the present invention:

For step b), a suitable amine is reacted at temperatures of from 4° C. to 150° C., preferably from 10° C. to 100° C. and particularly preferably from 20° C. to 80° C., with the products from step a). The molar ratio of primary amino groups to double bonds capable of addition is, for example, approximately from 1:1 to 1.1:1. Although the reaction can be catalysed with copper acetate, tin chloride or acetic acid, it is preferably carried out without the addition of a catalyst.

In general, the amines are fed under inert gas to the intermediate product from step a) placed in the reaction vessel and stirred at the mentioned temperatures for a period of from 1 hour to about 48 hours. Premixing of the amines with the intermediate product from step a) is likewise possible, for example via a mixing unit located in the common metering line. ("inline blending").

The progress of the reaction can be monitored by conventional methods, such as, for example, gas chromatographic analyses carried out online or offline or spectroscopic methods, such as, for example, NMR or IR spectroscopy. Traces of unreacted amines or any excess amities can be removed quantitatively after the reaction phase optionally in vacuo at an absolute pressure of from 1 to 500 mbar or by stripping.

The reaction of the components from step a) with the amine or amines in step b) can in principle take place in the same reactor as the preparation of the component according to step a). It is, however, preferred to carry out the reaction according to step b) in a different reactor, because traces of amine remaining in the reactor can impede the performance of the next DMC-catalysed step a).

It has been found to be advantageous to handle polyols for polyurethane (urea) applications quite generally always under an inert gas atmosphere. This is the case in particular for conventional alkaline polyether polyols, as are formed, for example, with alkali metal hydroxide catalysis before separation of the catalyst, or for products obtained with amine catalysis. Handling and storage with the exclusion of oxygen are also recommended for salt-free, worked up and stabilised intermediate and finished products or for intermediate and finished products prepared with DMC catalysis. The same is true for the hydroxy-amino polymers obtainable by the process according to the invention and their precursors obtainable according to step a). Suitable inert gases are, for example, noble gases, nitrogen or carbon dioxide; noble gases or nitrogen are particularly suitable. By preventing the ingress of oxygen, discolouration of the products can be avoided to the greatest possible extent; this is the case in particular at elevated temperatures, which are generally used to facilitate handling of the (intermediate) products by lowering the viscosity. Moreover, significantly fewer peroxide groups are also formed under an inert gas atmosphere; peroxide groups lead, with cleavage of the ether bonds, to the formation of further low molecular weight oxidative degradation products such as, for example, acetaldehyde, methanol, formic acid, formic acid esters, acetone and formaldehyde. Accordingly, the content of highly volatile organic compounds in the (intermediate) products can be lowered and odour nuisances, health detriments and losses of quality can be avoided.

The present invention relates further to a hydroxy-amino polymer obtainable by the process according to the invention, wherein the ratio of the amount of alkylene oxide compound to the amount of carboxylic acid anhydride is at least 1.1:1, preferably at least 2:1, particularly preferably at least 2.5:1, and wherein the hydroxy-amino polymer is more preferably not subjected to purification.

Particularly preferably, the hydroxy-amino polymer according to the invention has a structure according to the general formula (VII)

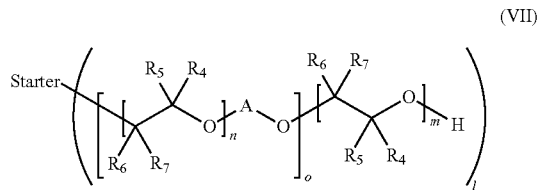

(VII)

wherein
"starter" represents the radical of the H-functional starter compound,
A represents an aspartate group having the following structure of formula (VIIIa) or (VIIIb)

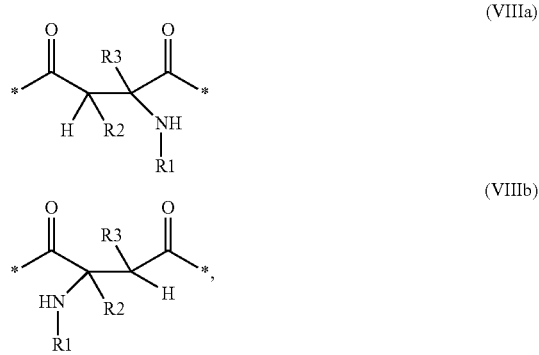

in which
R2 and R3 independently of one another represent hydrogen or an aliphatic or aromatic radical, and R2 and R3 may also be part of a cycloaliphatic ring system,
R1 represents hydrogen or an aliphatic, cycloaliphatic or aromatic radical which may also contain heteroatoms, in particular nitrogen atoms or oxygen atoms, as well as hydroxy groups,
R4, R5, R6 and R7 independently of one another represent hydrogen or an aliphatic or aromatic radical, and R5 and R6 may also be part of a cycloaliphatic ring system,
l represents the number of Zerewitinoff-active hydrogen atoms of the H-functional starter compound,
m, n and o are independent of one another and are integers, wherein n, o=0 or ≥1 and m≥2
and n, m are preferably from 2 to 430, in particular from 3 to 430, preferably from 4 to 430,
and o is preferably from 1 to 100, in particular from 1 to 50 and preferably from 1 to 10,
wherein the equivalent molar mass of the structure shown in formula VII does not exceed the value of 18,900 g/mol.

In the above-mentioned structure of formula VII, the variable number o can thus be chosen independently for each branch of the compound.

The present invention is additionally directed to a polyurethane urea polymer obtainable by reaction of a polyisocyanate with a hydroxy-amino polymer that can be prepared by the process according to the invention. To that end, the hydroxy-amino polymers obtainable by the process according to the invention can be reacted, alone or optionally in admixture with further isocyanate-reactive components, with organic polyisocyanates, optionally in the presence of foaming agents, catalysts and optionally further additives such as, for example, cell stabilisers, and can thus be used as components of solid or foamed polyurethane ureas. Consequently, the invention also provides polyurethane ureas, preferably solid or foamed polyurethane ureas, in particular coating systems comprising the hydroxy-amino polymers according to the invention.

Suitable polyisocyanates are aliphatic, cycloaliphatic, araliphatic, aromatic and heterocyclic polyisocyanates, as are described, for example, by W. Siefken in Justus Liebigs Annalen der Chemie, 562, pages 75 to 136, for example those of formula (IX)

(IX)

wherein
n=from 2 to 4, preferably 2 to 3,
and
Q denotes an aliphatic hydrocarbon radical having from 2 to 18, preferably from 6 to 10, carbon atoms, a cycloaliphatic hydrocarbon radical having from 4 to 15, preferably from 6 to 13, carbon atoms, or an araliphatic hydrocarbon radical having from 8 to 15, preferably from 8 to 13, carbon atoms.

For example, they are polyisocyanates as described in EF 0 007 502 A1, pages 7 to 8. Preference is generally given to the polyisocyanates that are readily accessible commercially, for example 2,4- and 2,6-toluene diisocyanate, as well as arbitrary mixtures of these isomers ("TDI"); polyphenyl-polymethylene polyisocyanates, such as are prepared by aniline-formaldehyde condensation and subsequent phosgenation ("crude MDI"), and polyisocyanates containing carbodiimide groups, urethane groups, allophanate groups, isocyanurate groups, urea groups or biuret groups ("modified polyisocyanates"), in particular those modified polyisocyanates which are derived from 2,4- and/or 2,6-toluene diisocyanate or from 4,4'- and/or 2,4'-diphenylmethane diisocyanate. The urethane-group-containing polyisocyanates (prepolymers) can be, for example, reaction products of the polyisocyanates with polyricinoleic acid ester polyols or any desired other polyols (for example conventional polyols). There is preferably used as the polyisocyanate at least one compound selected from the group consisting of 2,4- and 2,6-toluene diisocyanate, 4,4'- and 2,4'- and 2,2'-diphenylmethane diisocyanate and polyphenylpolymethylene polyisocyanate ("polynuclear MDI"); a mixture comprising 4,4'-diphenylmethane diisocyanate and 2,4'-diphenylmethane diisocyanate and polyphenylpolymethylene polyisocyanate is particularly preferably used as the polyisocyanate.

In addition to the above-mentioned polyisocyanates, conventional polyether polyols can additionally also be used for the preparation of the polyurethane (urea) polymers. Conventional polyether polyols within the meaning of the invention refers to compounds that are alkylene oxide addition products of starter compounds having Zerewitinoff-active hydrogen atoms, that is to say polyether polyols having a hydroxyl number according to DIN 53240 of from ≥3 mg KOH/g to ≤1000 mg KOH/g, preferably from ≥5 mg KOH/g to ≤600 mg KOH/g. Examples of such polyols are known to the person skilled in the art. They can have a hydroxyl number according to DIN 53240 of from ≥3 mg KOH/g to 1000 mg KOH/g, preferably from ≥5 mg KOH/g to ≤600 KOH/g. The starter compounds having Zerewitinoff-active hydrogen atoms used for the preparation of the conventional polyether polyols mostly have functionalities of from 2 to 8, preferably from 3 to 6, particularly preferably of 3, and the starter compounds are preferably hydroxy-functional. Examples of hydroxy-functional starter compounds are propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerol, trimethylolpropane, triethanolamine, pentaerythritol, sorbitol, sucrose, hydroquinone, pyrocatechol, resorcinol, bisphenol F, bisphenol A, 1,3,5-trihydroxybenzene, methylol-group-containing condensation products of formaldehyde and phenol or melamine or urea. Glycerol and/or trimethylolpropane is preferably used as the starter compound.

Suitable alkylene oxides for the conventional polyether polyols are, for example, ethylene oxide, propylene oxide, 1,2-butylene oxide or 2,3-butylene oxide and styrene oxide. Propylene oxide and ethylene oxide are preferably fed to the reaction mixture individually, in a mixture or in succession. If the alkylene oxides are metered in in succession, the products prepared contain polyether chains with block structures. Products with ethylene oxide blocks are characterised, for example, by increased concentrations of primary end groups, which impart advantageous isocyanate reactivity to the system.

Finally, the present invention is directed to the use of a hydroxy-amino polymer according to the invention in the preparation of a polyurethane urea polymer.

The present invention is explained in greater detail below with reference to exemplary embodiments.

Measurement and Determination Methods:

OH Number, Acid Number, Amine Number and Viscosity

Determination of the OH numbers was carried out as specified in DIN 53240. Determination of the acid numbers was carried out as specified in DIN EN ISO 2114. Determination of the amine numbers was carried out as specified in DIN 53176. The viscosities were determined by means of a rotary viscometer (Physica MCR 51, manufacturer: Anton Paar) as specified in DIN 53018 (spindle type CC27, shear rate range 16-128 $s^{-1}$).

Molar Mass Distribution

The molar mass distribution was determined by means of size exclusion chromatography (SEC). The device used was an Agilent 1100 Series from Agilent. The polydispersity PD for the molecular weight distribution $M_w/M_n$ is indicated, where $M_w$ denotes the weight-average molar mass and $M_n$ the number-average molar mass. Further information:
- column combination: 1 PSS precolumn, 5 µl, 8×50 mm; 2 PSS SVD, 5 µl, 100 A°, 8×300 mm; 2 PSS SVD, 5 µl, 1000 A°, 8×300 mm; PSS is the manufacturer of the columns (Polymer Standard Solutions, Mainz)
- evaluation software: WIN GPC from PSS
- solvent: THF (Merck LiChrosolv)
- flow rate: 1 ml/min
- detector type: RI detector (refractive index), Shodex RI 74
- calibration standards used: polystyrene-based PSS calibration standard.

Raw Materials Used

Catalyst for the Alkylene Oxide/Acid Anhydride Addition (DMC Catalyst):

Double metal cyanide catalyst comprising zinc hexacyanocobaltate, tert-butanol and polypropylene glycol having a number-average molecular weight of 1000 g/mol; described in WO 0180994 A1, Example 6.

Ambosol®: precipitated, colloidal, synthetically prepared magnesium silicate, acquired from PQ Europe.

Polyol A: polyether obtained by addition of ethylene oxide to propylene glycol with KOH catalysis; OH number: 190 mg KOH/g, number-average molar mass: 591 g/mol

EXAMPLE

A) Preparation of an Alkylene Oxide/Maleic Anhydride Copolymer by DMC Catalysis (Prepolymer According to Step a))

233.7 g (396 mmol) of polyol A and 0.25 g of 85% phosphoric acid were placed in a 2-liter laboratory autoclave under a nitrogen atmosphere and stirred for 30 minutes at room temperature (propeller stirrer at 800 rpm). After addition of 0.601 g of DMC catalyst, the contents of the autoclave were stripped for 30 minutes at 130° C. and with stirring (propeller stirrer) at 450 rpm at an absolute pressure of from 100 to 120 mbar with the introduction of 50 ml of nitrogen per minute via a distributor ring located beneath the liquid level. At 130° C. and with stirring at 800 rpm, a mixture of 156.5 g of propylene oxide and 469.7 g of ethylene oxide was metered into the head space of the autoclave, over a period of 2.02 hours, the metering was started at an absolute pressure of 0.05 bar. After a post-reaction time of 20 minutes, the mixture was cooled to room temperature and 0.627 g of vitamin E and 77.9 g (794 mmol) of maleic anhydride were added to the autoclave. Residual oxygen was removed, after closing of the filling nozzle, at 25° C. by applying an oxygen pressure four times up to an absolute pressure of 4 bar and then relieving the excess pressure to atmospheric pressure. After heating to 80° C., a mixture of 65.6 g of propylene oxide and 197.0 g of ethylene oxide was metered into the head space of the autoclave over a period of 2.65 hours. After a post-reaction time of 30 minutes, the product was heated for 30 minutes at 80° C. at an absolute pressure of 10 mbar; 0.214 g of vitamin E was then added.

1102.4 g of the intermediate product were introduced into a 2-liter three-necked flask. After evacuation and relief with nitrogen three times, 88.2 g of Ambosol® were added in a nitrogen countercurrent at 80° C. The contents of the flask were stirred at 80° C. over a period of 3 hours, and heating was then carried out for a further 3 hours at 80° C. and an absolute pressure of 1 mbar. The Ambosol® was then separated off by filtration over a laboratory suction filter heated with a stream of steam (about 100° C.).

The resulting intermediate product had a viscosity of 1854 mPas at 25° C., an OH number of 38 mg KOH/g and an acid number of 10 ppm KOH. A polydispersity (Mw/Mn) of 1.38 was determined by size exclusion chromatography. Such a low polydispersity cannot be achieved with an unsaturated polyester prepared by polycondensation reaction, because the molar masses of products so prepared are subject to Schultz-Flory distribution, whereas the intermediate products prepared by the process according to the invention by DMC catalysis exhibit significantly narrower Poisson distributions.

B) Reaction of the Intermediate Product from A) with N-butylamine (Step b))

100 g (33.8 mmol) of the intermediate product from step A) were introduced into a 500 ml 4-necked flask fitted with a reflux condenser, an internal thermometer and a magnetic stirrer. After evacuation and letting off with nitrogen three times, 5.0644 g (69.2 mmol) of N-butylamine were added in a nitrogen countercurrent. Within a few minutes, the internal temperature of the flask rose from 26° C. to 34° C. After 30 minutes, the internal temperature of the flask had risen to 60°

C. by means of a heating mantle and was maintained at that temperature for 4 hours with stirring.

The viscosity of the product was 1633 mPas at 25° C. The measured "OH number" was 73.4 mg KOH/g, the measured "OH number" in this specific case being the sum of the amine number and the actual OH number. The amine number was 35 mg KOH/g, which corresponds to about half of the measured "OH number". The stoichiometry of the MSA incorporation in the precursor had been so chosen that 1 MSA per OH group was used. The result shows that virtually all the double bonds had reacted.

The invention claimed is:

1. A process for the preparation of a hydroxy-amino polymer, comprising:
    a) reacting an H-functional starter compound which has at least one Zerewitinoff-active H atom with an unsaturated cyclic carboxylic acid anhydride and one or more of alkylene oxide compounds to form a hydroxyl-group-containing prepolymer,
    b) adding a compound selected from the group consisting of primary amine group containing compounds, ammonia and mixtures thereof to the double bonds of the hydroxyl-group-containing prepolymer a) to yield the hydroxy-amino polymer,
    wherein
    the reaction of said H-functional starter compound with said unsaturated cyclic carboxylic acid anhydride and/or the addition of said alkylene oxide compound is carried out in the presence of a double metal cyanide catalyst (DMC catalyst), said H-functional starter compound contains from 1 to 35 Zerewitinoff-active H atoms,
    said alkylene oxide compounds are chosen from alkylene oxides having from 2 to 24 carbon atoms,
    said alkylene oxide compounds present in step a) comprise ethylene oxide in an amount greater than 50 wt. % of the total alkylene oxide compounds,
    the molar ratio of the amount of alkylene oxide compounds to the amount of carboxylic acid anhydride is at least 1.1:1,
    said H-functional starter compound and said DMC catalyst are first placed in a reaction vessel, alkylene oxide compound and optionally comonomer are metered in, and then said unsaturated cyclic carboxylic acid anhydride is added, and after the addition of said unsaturated cyclic carboxylic acid anhydride has taken place, alkylene oxide compound and optionally further comonomer are metered in again, and
    said primary amine group containing compound has at least one primary amine group and optionally contains hydroxyl groups, and is selected from the group consisting of aliphatic monoamines, aliphatic diamines, cycloaliphatic monoamines, cycloaliphatic diamines, araliphatic monoamines and araliphatic diamines.

2. The process according to claim 1, wherein said H-functional starter compound has a number-average molar mass of from 17 to 1200 g/mol.

3. The process according to claim 1, wherein said unsaturated cyclic carboxylic acid anhydride is an unsaturated cyclic dicarboxylic acid anhydride.

4. The process according to claim 1, wherein at least one comonomer is additionally reacted in a), and said comonomer is selected from the group consisting of lactones, lactides, saturated cyclic carboxylic acid anhydrides, aromatic cyclic carboxylic acid anhydrides, cyclic carbonates, carbon dioxide and mixtures thereof, wherein the reaction of said comonomer is catalysed by the DMC catalyst.

5. The process according to claim 1, wherein the ratio of the amount of carboxylic acid anhydride to the number of Zerewitinoff-active H atoms of said H-functional starter compound is approximately from 1:1 to 1.5:1.

6. The process according to claim 1, wherein said H-functional starter compound and said DMC catalyst are first placed in a reaction vessel, and then said alkylene oxide compound, said cyclic unsaturated carboxylic acid anhydride and optionally said comonomer are added.

7. The process according to claim 1, wherein said H-functional starter polyol comprises a hydroxyl-group containing prepolymer which is formed by reacting an H-functional starter compound which has at least one Zerewitinoff-active H atom with an unsaturated cyclic carboxylic acid anhydride and at least one alkylene oxide compound.

8. The process according to claim 6 wherein the metering of the cyclic carboxylic acid anhydride is terminated before the alkylene oxide compound is metered in, and in a final metering of alkylene oxide and, optionally a comonomer, more than 1 mol of alkylene oxide compound is metered in per mol of Zerewitinoff-active hydrogen is metered in.

9. The process according to claim 1, wherein in step a), an H-functional starter polyol and a partial amount of the DMC catalyst are placed in the reactor system; the H-functional compound and further DMC catalyst are fed in continuously together with the alkylene oxide and the unsaturated cyclic carboxylic acid anhydride; wherein the resulting reaction product of a) is continuously removed from the reactor system after a preselectable mean residence time.

10. A hydroxy-amino polymer obtainable by the process according to claim 1, wherein the ratio of the amount of alkylene oxide compound to the amount of carboxylic acid anhydride is at least 1.1:1, and wherein the hydroxy-amino polymer is not subjected to purification.

11. The hydroxy-amino polymer according to claim 10, wherein said hydroxy-amino polymer has a structure corresponding to the general formula (VII)

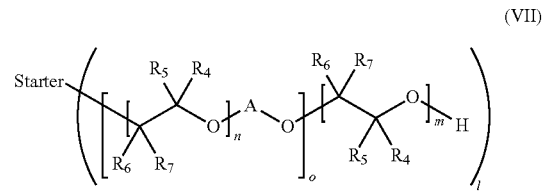

wherein

"starter" represents the radical of the H-functional starter compound,

A represents an aspartate group corresponding to formula (VIIIa) or (VIIIb)

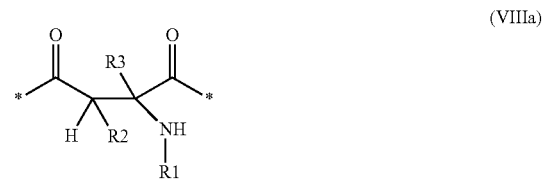

-continued

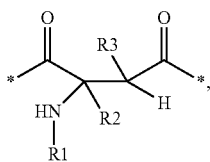
(VIIIb)

wherein

R2 and R3 independently of one another represent hydrogen, an aliphatic radical, an aromatic radical, or R2 and R3 may be part of a cycloaliphatic ring system, R1 represents hydrogen, an aliphatic radical which may contain heteroatoms, a cycloaliphatic radical which may contain heteroatoms or an aromatic radical which may also contain heteroatoms, R4, R5, R6 and R7 independently of one another represent hydrogen, an aliphatic radical, an aromatic radical, or R5 and R6 may be part of a cycloaliphatic ring system, l represents the number of Zerewitinoff-active hydrogen atoms of the H-functional starter compound, m, n and o are independent of one another and are integers, wherein n and o=0 or ≥1, and m≥2, wherein the equivalent molar mass of the compound corresponding to the structure shown in formula VII does not exceed the value of 18,900 g/mol.

12. A polyurethane urea polymer obtainable by reaction of a polyisocyanate with the hydroxy-amino polymer according to claim 10.

13. The process according to claim 1, wherein the alkylene oxide compounds further comprise propylene oxide.

14. The process according to claim 1, wherein the alkylene oxide compounds present in step a) comprise ethylene oxide in an amount greater than 60 wt. % of the total alkylene oxide compounds.

15. The process according to claim 14, wherein the alkylene oxide compounds further comprise propylene oxide.

* * * * *